(12) United States Patent
Mijers

(10) Patent No.: US 6,708,714 B1
(45) Date of Patent: Mar. 23, 2004

(54) TWO-WAY VALVE, ESPECIALLY FOR LIQUID DISPENSERS

(75) Inventor: Jan Willem Marinus Mijers, Venlo (NL)

(73) Assignee: Ing. Erich Pfeiffer GmbH, Radolfzell (DE)

( * ) Notice: Subject to any disclaimer, the term of this patent is extended or adjusted under 35 U.S.C. 154(b) by 81 days.

(21) Appl. No.: 10/019,759
(22) PCT Filed: Jun. 28, 2000
(86) PCT No.: PCT/EP00/06023
§ 371 (c)(1), (2), (4) Date: Dec. 27, 2001
(87) PCT Pub. No.: WO01/01023
PCT Pub. Date: Jan. 4, 2001

(30) Foreign Application Priority Data

Jun. 28, 1999 (DE) .......................... 199 29 607

(51) Int. Cl.⁷ ............................................... F16K 15/14
(52) U.S. Cl. ..................... 137/102; 222/213; 222/494; 251/359
(58) Field of Search .................. 137/102; 251/331, 251/359; 222/213, 494

(56) References Cited

U.S. PATENT DOCUMENTS

| | | |
|---|---|---|
| 3,270,771 A | 9/1966 | Morgan et al. |
| 3,460,558 A | 8/1969 | Johanisson |
| 4,084,606 A | 4/1978 | Mittleman |
| 4,246,932 A | 1/1981 | Raines |
| 5,848,881 A  * | 12/1998 | Frezza ................ 137/102 X |

FOREIGN PATENT DOCUMENTS

| | | |
|---|---|---|
| DE | 1 600 930 | 1/1972 |
| DE | 25 18 091 A1 | 11/1975 |
| DE | 40 39 814 A1 | 6/1992 |
| DE | 43 04 949 A1 | 8/1994 |
| DE | 196 43 360 C1 | 5/1998 |
| DE | 198 16 398 A1 | 10/1999 |
| FR | 2 666 745 A1 | 3/1992 |

OTHER PUBLICATIONS

International Search Report for PCT/EP 00/06023, dated Nov. 29, 2000.

* cited by examiner

*Primary Examiner*—Kevin Lee
(74) *Attorney, Agent, or Firm*—Quarles & Brady LLP

(57) ABSTRACT

The invention relates to a two-way valve, especially for liquid dispensers. The inventive valve comprises connections (1,2,3) for a liquid reservoir (1a), for a pump and for a liquid consumer. A membrane disk (4) is clamped between a valve housing (5) and a cover housing (6) and lies flat against a surface of a ring seat (10) in whose range (7) an axial opening (8) is located. Said membrane disk (4), at the cover end, lies flat against the surface of a counter ring seat (6a) that has the same diameter. The aim of the invention is to provide, based on a two-way valve, a system with a spring-loaded piston that deviates from the steel ball compression spring system. To this end, an additional two-side gripping (9) of the membrane disk (4) is used that consists of the surface of the counter ring seat (6a) and the surface of a ring seat (2a). In addition to this supplementary clamping (9) a first ring channel (11) is configured which opens into the third connection.

8 Claims, 3 Drawing Sheets

TWO-WAY VALVE, ESPECIALLY FOR LIQUID DISPENSERS

BACKGROUND OF THE INVENTION

The invention relates to a two-way valve, particularly for a liquid dispenser, having a first connection for a liquid reservoir, a second connection for a pump for suction or compression and a third connection for a liquid consuming means, a diaphragm disk being clamped at its radially outer annular edge between a valve housing and a cover housing and engages flat against an annular seat, in whose vicinity is located an axial opening for the liquid and on which on the cover side the diaphragm disk engages against a mating annular seat having the same diameter.

Such a two-way valve is known from an earlier dated, but not previously published DE 198 16 398 A1 having a first connection for a medicament reservoir, a second connection for a suction or compression pump (with piston) and a third connection for a liquid consuming means. A similar construction can be gathered from U.S. Pat. No. 4,246,932.

DE 196 43 360 C1 discloses a diaphragm disk clamped with a full cross-section on its radially outer annular edge between a valve housing and a cover housing and which is engaged against an annular seat. In the vicinity of the annular seat is provided an axial opening for the liquid and on the cover side the diaphragm disk rests against another annular seat.

Such two-way valves are used in the medicine and hygiene fields e.g. for infusers, spray containers, etc. or in liquid dispensers for liquid soaps, creams, suspensions of all types, cleaning agents, detergents, gels, ointments, etc. The term liquid is here understood to cover all types of fluids, particularly also suspensions of solids in fluids and gels, foams, etc.

The pump systems used for this purpose are in each case based on a unit constituted by a connecting piece, sealing housing, piston with compression spring and a ball. Since for weight and cost reasons the balls are made from steel or stainless steel, undesired physicochemical reactions occur between the liquid and the steel material, so that when a medicament comes into contact with the ball molecular processes occur, which modify the medicament and consequently prevent the use of such a system.

SUMMARY OF THE INVENTION

Diverging from the known steel ball-compression spring system and based on two-way valves with diaphragm disks, the problem of the invention is to provide a two-way valve with spring-loaded piston through which individual portions can be metered and discharged.

According to the invention the set problem is solved in that between the radially outer annular edge and a radially smaller diameter annular seat is provided an additional bilateral clamping of the centrally open diaphragm disk, comprising the mating annular seat and an annular seat and that in addition to the additional clamping of the first connection a first annular channel is formed, which issues into the third connection. Thus, during a suction stroke of the piston the liquid is sucked and by a following compression stroke is conveyed through the third connection for the liquid consuming means. Liquid transport can take place in matched quantities as a function of the viscosity of the liquid.

According to a development, between the radially outer annular edge of the diaphragm disk and the additional, radially inner clamping, the diaphragm disk engages against a unilateral, valve housing-side, annular bearing surface, so that a further valve seat is created, so that in principle two valves are combined in the two-way valve.

According to other features, the annular bearing surface on the valve housing is faced by an annular channel of the cover housing. The advantage is the creation of an adequately large volume flow channel.

According to a further development, within the valve housing and radially adjacent to the bearing surface, is provided a connection channel facing the annular channel of the cover housing. The connection channel ensures an adequately large flow-connection for removing the liquid in the third connection.

The provision of an adequately large flow cross-section is helped by the fact that on the side of the valve housing the annular connection channel has an axial length greater than the radial width. The greater axial length corresponds to the diameter of the flow channel in the third connection.

The provision of favourable flow cross-sections is also helped by the fact that at a circumferential point the annular channel is connected by a channel section in the cover housing surrounding the diameter of the diaphragm disk and a similar channel section in the valve housing to the connection channel. This measure also helps to create an independent flow channel for the piston compression process.

According to an improvement, within the cover housing the annular seat is formed by means of an inwardly hollow recess of a core part of the cover housing, which creates the aforementioned annular seat for the diaphragm disk.

According to further features of the invention around the core part of the cover housing are arranged individual annular segmental recesses or several cylindrical holes, which link the first connection to the centre when the valve is open.

BRIEF DESCRIPTION OF THE DRAWINGS

Embodiments of the invention are described in greater detail hereinafter relative to the attached drawings, wherein show.

DETAILED DESCRIPTION OF THE INVENTION

Figure 1A:
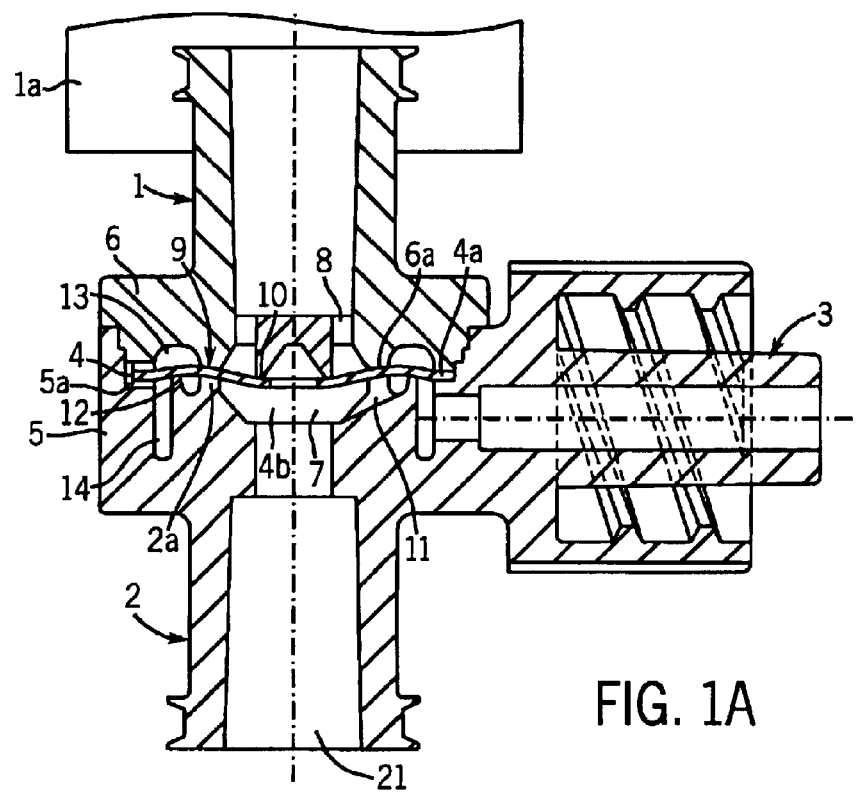
FIG. 1A An axial cross-section through the two-way valve in the suction position.

The two-way valve is provided with a first connection 1 for a liquid reservoir 1*a* and a second connection 2 for a not shown pump. The pump can comprise a single piston, which is operated manually. There is also a third connection 3 for the liquid consuming means. The latter can be a patient to whom a medicamentous liquid is to be administered. As shown, the third connection 3 is constructed as a Luer-Lock connection. The essential component of the two-way valve is a diaphragm disk 4, which at its radially outer annular edge 4*a* is clamped between a valve housing 5 and a cover housing 6, which are permanently and tightly interconnected e.g. by welding together the plastic parts. The shape of the connections 1, 2, 3 can be of a random nature. For medical and medico-technical applications use can e.g. be made of Luer-Lock connections. The connections can be both male and female connections. The diaphragm disk 4 engages against an annular seat 10, which is brought about by a special design. In the vicinity 7 of the annular seat 10 is provided an axial opening 8 for the liquid to be sucked and which is subsequently supplied through the third connection 3 to the liquid consuming means. The diaphragm disk 4 on the cover side engages against a mating annular seat 6a of the same diameter.

For the suction stroke such a two-way valve forms a passage from the liquid reservoir 1a into a cylinder chamber 21 and then for the compression stroke of the piston a passage into the third connection 3.

These passages are made possible in that between the radially outer annular edge 4a of the diaphragm disk 4 and a radially smaller diameter annular seat 10 is created an additional, bilateral clamping 9 of the diaphragm disk 4 which is open in the centre 4b and which comprises the mating annular seat 6a and an annular seat 2a. Besides the actual clamping 9 on the radially outer annular edge 4a of the first connection 1 is formed a first annular channel 11 which, when the valve is open, issues into the third connection 3.

Figure 3:
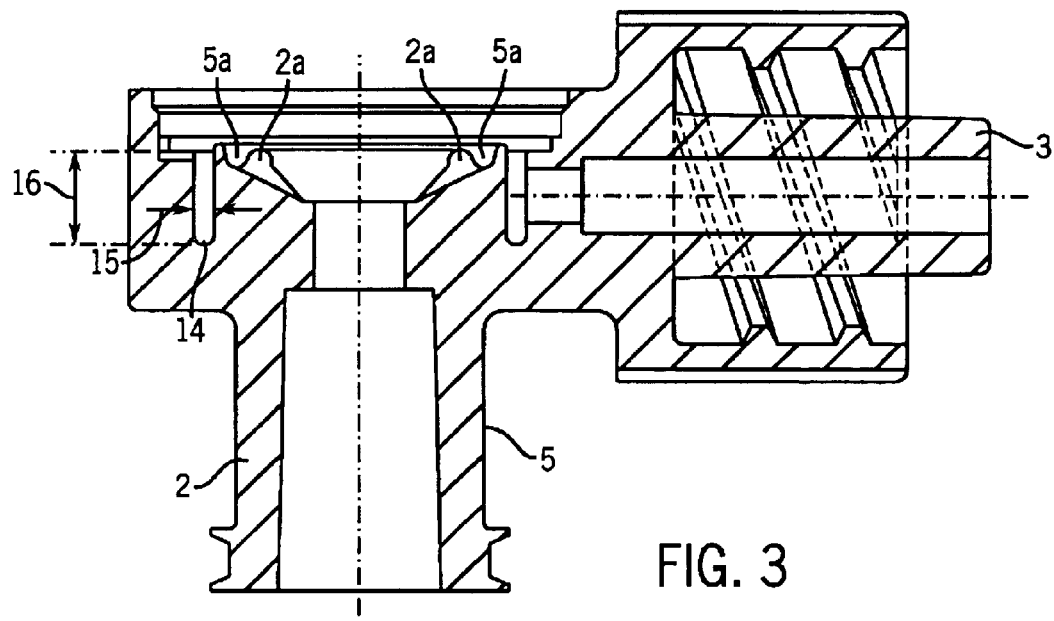
FIG. 3 An axial cross-section according to FIG. 1 through the valve housing.

Between the radially outer annular edge 4a of the diaphragm disk 4 and the additional, radially inner clamping 9 the diaphragm disk 4 engages against a unilateral, valve housing-side, annular bearing surface 12. A second annular channel 13 of the cover housing 6 faces the annular bearing surface 12 on valve housing 5. Radially adjacent to the bearing surface 12 is provided within the valve housing 5 a connection channel 14 facing the annular channel 13 of the cover housing 6. The annular connection channel 14, which is formed in the valve housing 5 by the injection moulding of plastic, has a greater axial length 16 as compared with the radial width 15 (cf. FIG. 3).

Figure 4:
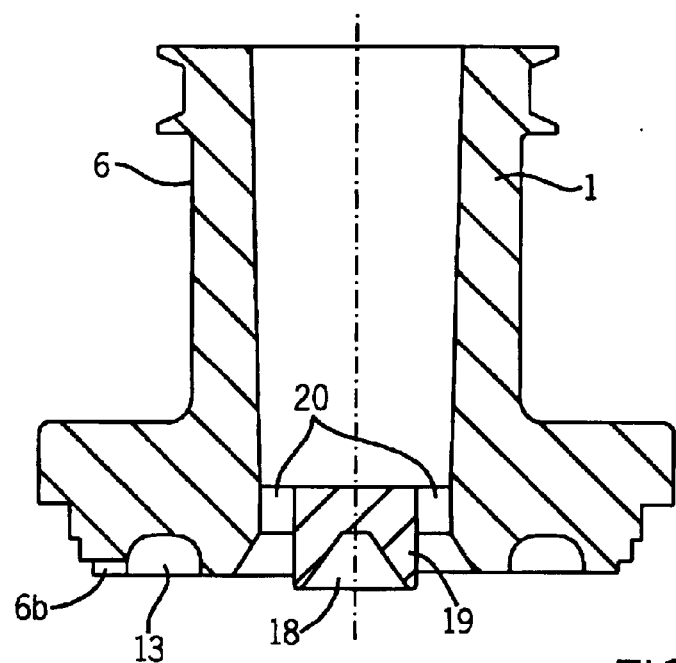
FIG. 4 An axial cross-section through the cover housing.
Figure 5:
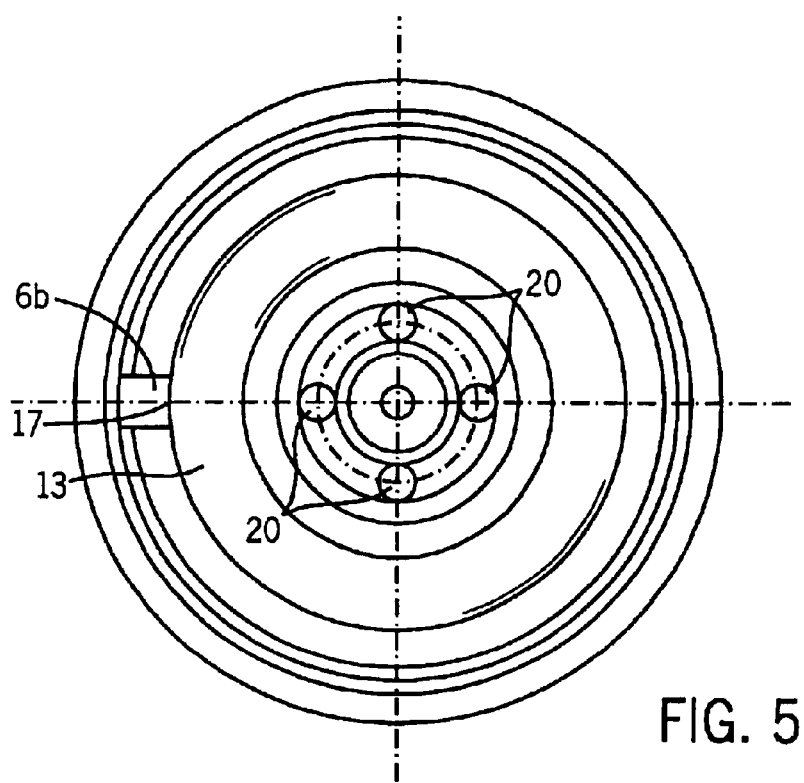
FIG. 5 A plan view of the cover housing of FIG. 4.

At a circumferential point 17, the second annular channel 13 is connected by a channel section 6b (cf. also FIG. 4) in the cover housing 6 surrounding the diameter of the diaphragm disk 4 and a supplementary channel section 5a in the valve housing 5 to the connection channel 14. In the valve housing 5 the annular seat 10 is formed by means of an inwardly hollow recess 18 of a core part 19 of the cover housing 6. Around the core part 19 are provided individual, ring segmental recesses or (as shown) several cylindrical holes 20, which link the cylinder chamber 21 for a suction/compression piston in the vicinity 7 to the first annular channel 11.

The diaphragm disk 4 is pretensioned against the annular seat 10 and the annular bearing surface 12. The pretension with respect to the annular seat 10 and the annular bearing surface 12 ensures that there is a leak-free seal of the two-way valve both to the inside and to the outside. The pretension is also advantageous with respect to the annular bearing surface 12 because the possibility exists of establishing a supply pressure for dischargeable liquids. It is necessary for overcoming the pretension with respect to the annular bearing surface 12 that the liquid to be discharged is under a correspondingly higher pressure. The higher the pretension, the higher the supply pressure necessary before a discharge takes place. Thus, particularly when using the valve combined with a spraying nozzle an adequate spraying pressure is obtained in the liquid to bring about a uniform, satisfactory atomization.

The diaphragm disk 4 is advantageously made from an elastic material. It is possible to use both natural rubber, silicone rubber, synthetic elastomers and thermoplastic elastomers. In particular, the use of thermoplastic elastomers is advantageous, because they can be processed in the same way as thermoplastic polymers (e.g. injection moulding), but have elastomeric characteristics which are at least equivalent to those of natural rubber, synthetic elastomers or silicone rubber. It is particularly advantageous to use a two-component injection moulding process for producing the diaphragm disk 4. It is then possible to produce a diaphragm disk 4 which comprises two rings having a different spring temper. Thus, e.g. the outer ring can have harder spring characteristics than the softer inner ring. Thus, e.g. the outer ring could have a Shore hardness of approximately A90 and the inner ring a Shore hardness of approximately A35. The above values concerning the Shore hardness are of an exemplified nature. The Shore hardness of the individual ring must be chosen as a function of the conditions of the individual valve and the desired initial stressing forces with respect to the annular bearing support 12 and the annular seat 10. Nevertheless the appropriate choice of the hardness of the corresponding ring makes it possible to regulate the suction and compression pressure during the discharge stroke in such a way that the atomizer or dispenser function can be optimized.

For many applications it can be advantageous if the leak tightness of the two-way valve is also ensured in the case of a vacuum. For the above described valve it is possible to ensure leak tightness down to pressures of approximately 300 mbar, if no use is made of the channel section 6b. If as a result of a low external pressure, e.g. due to the use of the valve or liquid dispenser in the interior of an aircraft, there is a vacuum on the outside, due to the fluidic connection of the connection channel 14 with the third connection 3 a vacuum also occurs there. The part of the diaphragm disk 4, which engages on the valve housing-side, annular bearing surface 12, is more strongly pressed as a result of the pressure difference between the second annular channel 13 and the reduced pressure in the connection channel 14. However, in the centre 4b the same higher pressure prevails as in the second annular channel 13. Since, however, the surface of the annular channel 13 with the higher pressure is larger than the first annular channel 11, the compressive force acting in the inwardly closing sense is also higher than the opposing force with respect to the pressure in the annular channel 13. Therefore the two-way valve is still sealed if it has to operate and seal against an externally applied vacuum.

The operation of the two-way valve will now be described:

During a downward suction stroke of the piston in cylinder chamber 21 (FIG. 1A), liquid flows through the first connection 1 and through the centrally open diaphragm disk 4 into the cylinder chamber 21. The flow gap on the annular seat 10 results from the suction force built up in the centre 4b and in the hollow recess 19.

Figure 1B:
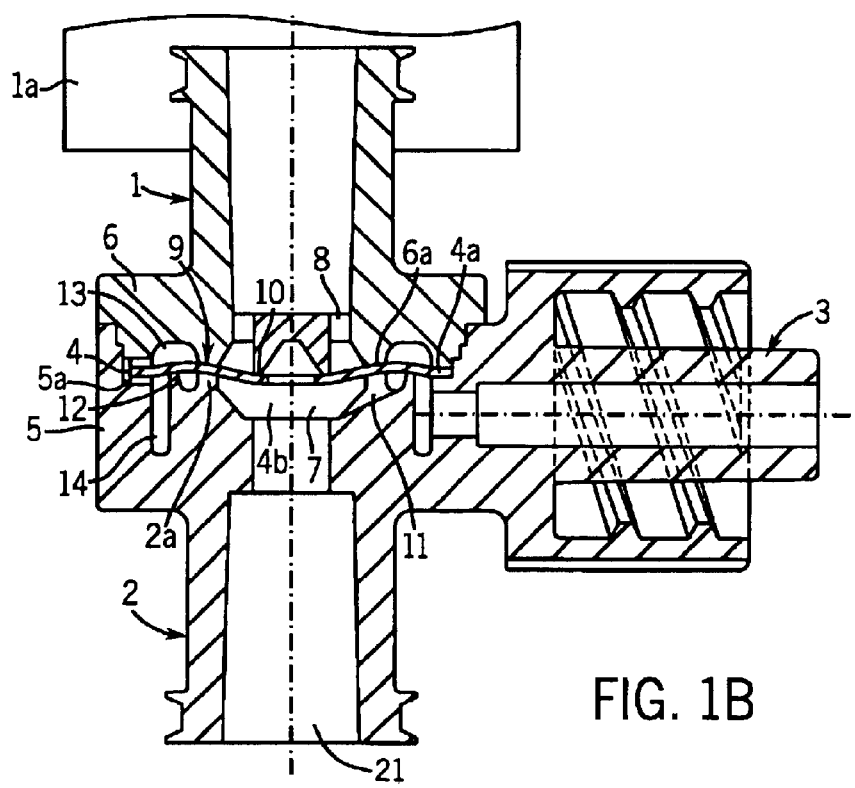
FIG. 1B An axial cross-section through the two-way valve in the compression position.
Figure 2:
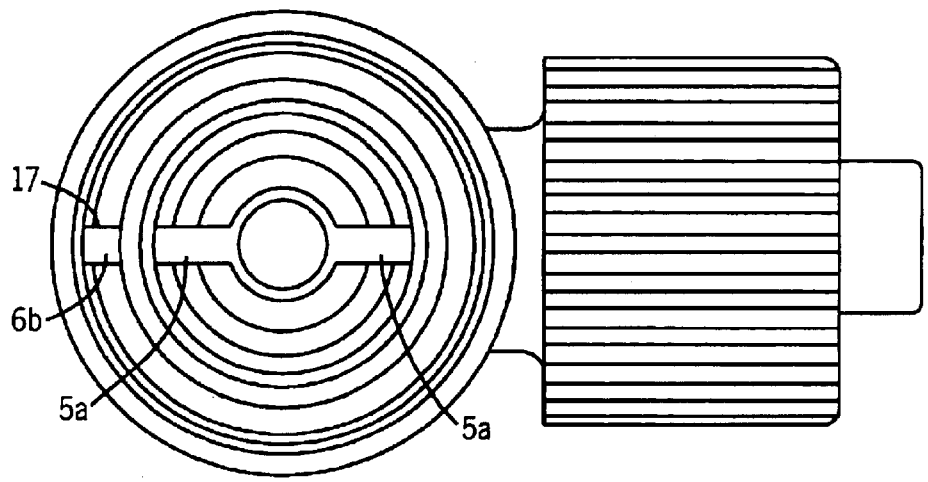
FIG. 2 A plan view of the valve housing shown without the cover housing.

After reversing the piston movement in the vertically upward direction (FIG. 1B), the liquid presses through the centre 4b onto the larger annular surface of the annular bearing support 12, which exists between the additional clamping 9 and the radial annular edge 4a.

With regards to the pretension with which the diaphragm disk 4 bears on the cover-side, annular bearing surface 12, the pressure prevailing there is sufficient to obtain an opening of the diaphragm disk 4, the pressure propagating into the connection channel 14. On sucking the liquid, as a result of the large diameter, the diaphragm disk 4 is linked to the coverside, annular bearing surface 12.

What is claimed is:

1. Two-way valve, particularly for liquid dispensers, with a first connection for a liquid reservoir, a second connection for a pump for suction or compression and a third connection for a liquid consuming means, a diaphragm disk being clamped on its radially outer annular edge between a valve housing and a cover housing and engaging flat against an annular seat, in whose vicinity is located an axial opening for the liquid and where the diaphragm disk engages on the cover side against a mating annular seat having the same diameter, characterized in that between the radially outer annular edge (4a) and a radially smaller diameter annular seat (10) is provided an additional, bilateral clamping (9) of the diaphragm disk (4) open in the centre (4b) and which comprises the mating annular seat (6a) and an annular seat (2a) and that besides the additional clamping (9) a first annular channel (11) is formed, which issues into the third connection (3).

2. Two-way valve according to claim 1, characterized in that between the radially outer annular edge (4a) of the diaphragm disk (4) and the additional, radially inner clamping (9), the diaphragm disk (4) engages against a unilateral, valve housing-side., annular bearing surface (12).

3. Two-way valve according to claim 1, characterized in that an annular channel (13) of the cover housing (6) faces the annular bearing surface (12) on the valve housing (5).

4. Two-way valve according to claim 1, characterized in that, radially adjacent the bearing surface (12), within the valve housing (5) is provided a connection channel (14) facing the annular channel (13) of the cover housing (6).

5. Two-way valve according to one of the claim 1, characterized in that on the side of the valve housing (5), the annular connection channel (14) is provided with an axial length (16) larger than the radial width (15).

6. Two-way valve according to claim 1, characterized in that at a circumferential point (17), the annular channel (13) is connected by a channel section (6b) in the cover housing (6) surrounding the diameter of the diaphragm disk (4) and a similar channel section (5a) in the valve housing (5) to the connection channel (14).

7. Two-way valve according to one of claim 1, characterized in that the annular seat (10) in the cover housing (6) is formed by means of an inwardly hollow recess (18) of a core part (19) of the cover housing (6).

8. Two-way valve according to claim 1, characterized in characterized in that individual ring segmental recesses or several cylindrical holes (20) are arranged around the core part (19) of the cover housing (6) and link the first connection (1) to the center (4b) when the valve is open for liquid suction purposes.

* * * * *